United States Patent [19]

Buechler et al.

[11] Patent Number: 5,302,715

[45] Date of Patent: Apr. 12, 1994

[54] BENZODIAZEPINE DERIVATIVES

[75] Inventors: Kenneth F. Buechler, San Diego; Joseph B. Noar, Solana Beach, both of Calif.

[73] Assignee: Biosite Diagnostics, Inc., San Diego, Calif.

[21] Appl. No.: 864,093

[22] Filed: Apr. 6, 1992

[51] Int. Cl.$^5$ .................... C07D 243/24; A61K 31/55
[52] U.S. Cl. .................................... 540/507; 540/512
[58] Field of Search .............................. 540/508, 514

[56] References Cited

U.S. PATENT DOCUMENTS 3,757,008  9/1973  Hellerbach et al. ................ 540/514

Primary Examiner—Robert T. Bond
Attorney, Agent, or Firm—Lyon & Lyon

[57] ABSTRACT

The present invention is directed to novel benzodiazepine derivatives which are synthesized for the covalent attachment to antigens (proteins or polypeptides) for the preparation of antibodies or receptors to the benzodiazepine metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

4 Claims, 1 Drawing Sheet

EXAMPLE 1

EXAMPLE 5

EXAMPLE 2

EXAMPLE 6

EXAMPLE 3

EXAMPLE 7

BENZODIAZEPINE DERIVATIVES

FIELD OF THE INVENTION

This invention is in the field of ligand receptor assays, including immunoassays, for the detection of selected metabolites of benzodiazepines in a fluid sample. More particularly, this invention relates to methods for the synthesis of novel benzodiazepine derivatives and protein and polypeptide benzodiazepine derivative conjugates and labels for use in the preparation of antibodies to benzodiazepine metabolites and for use in the immunoassay process.

BACKGROUND OF THE INVENTION

Benzodiazepines are a class of drugs which possess sedative and tranquilizing properties. The benzodiazepines are used clinically to treat a variety of ailments, including depression, anxiety, insomnia and muscle spasms. The class of benzodiazepines include alprazolam, bromazepam, clonazepam, diazepam, flunitrazepam, flurazepam, halazepam, lorazepam, medazepam, nitrazepam, oxazepam, prazepam, quazepam, temazepam and triazolam. The abuse of benzodiazepines has prompted a need to monitor the concentration in urine. Benzodiazepines are metabolized to a variety of derivatives and the majority of the metabolites are excreted in the urine as glucuronides, for example, see Clin. Pharm. Ther. 19, 443 (1976), Arz. Forsch. 22, 687 (1972) and Clin. Pharm. Ther. 20, 329 (1976).

The preparation of antibodies to benzodiazepine metabolites requires the synthesis of a benzodiazepine derivative in order to covalently attach the derivative to an antigenic polypeptide or protein. In addition, the benzodiazepine derivative is covalently attached to various polypeptides, proteins or labels for use in screening antibodies and in the immunoassay process. The benzodiazepine derivative should mimic the structure of the benzodiazepine metabolite sought to be measured. Therefore, the selection and synthesis of the types of benzodiazepine derivatives for covalent attachment to proteins, polypeptides or labels is critical. In addition, the benzodiazepine derivatives need to be stable and soluble in an aqueous solution.

Benzodiazepine compounds and conjugates for immunization and immunoassay have been described in U.S. Pat. Nos. 4,046,636, 4,083,948, 4,243,654 and 4,869,895.

SUMMARY OF THE INVENTION

The present invention is directed to novel benzodiazepine derivatives which are synthesized for the covalent attachment to antigens (proteins or polypeptides) for the preparation of antibodies to the benzodiazepine metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids and tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the composition between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1-20 carbons and 0-10 heterocarbons (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definitions section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the $-C_6H_4-Ar$ substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups $-NRR'$ wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO— or HCO—.

The terms "acylamino" refers to RCONCR)— and (RCO$_2$N— respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonymethyl" refers to hydrocarbyl—OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl—O—CONR- wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methene" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
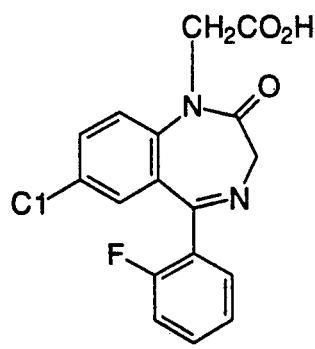
FIG. 1 depicts the structures of the compounds of Examples 1-7.
Figure 1:
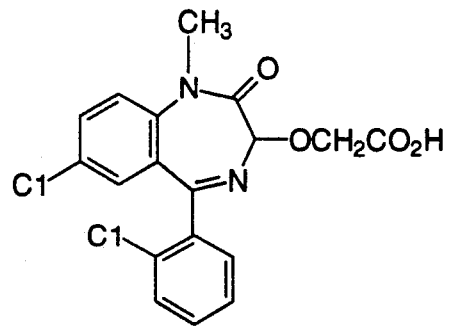
Figure 1:
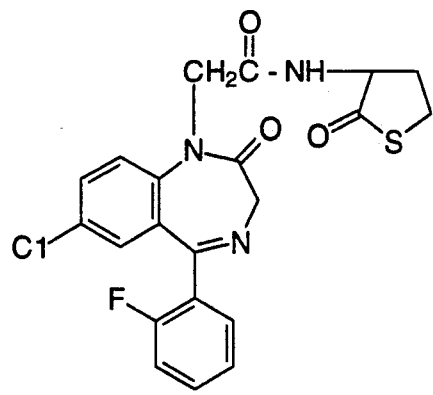
Figure 1:
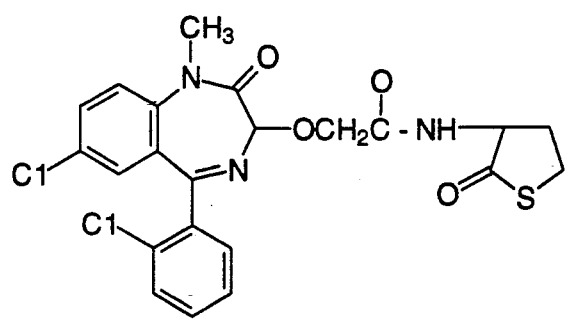
Figure 1:
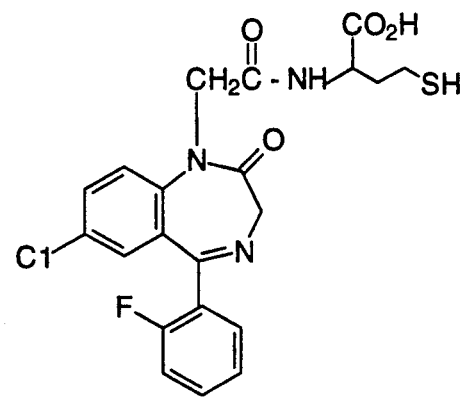
Figure 1:
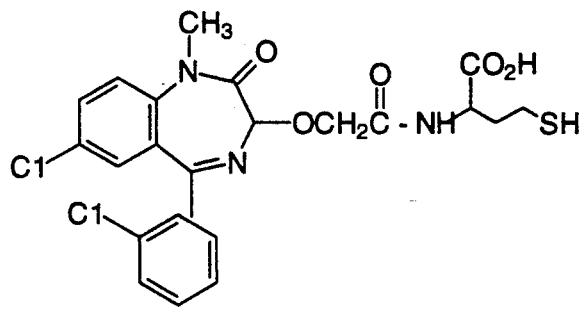

Novel compounds are described which are used in the generation of antibodies and in the immunoassay process generally. The compounds are derivatives of benzodiazepine metabolites. The derivatization of the benzodiazepine analogue for covalent attachment to proteins, polypeptides and labels occurs on either the amide nitrogen or the 3' hydroxyl position. The synthesis of the linking group between the protein, polypeptide or label and the benzodiazepine derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

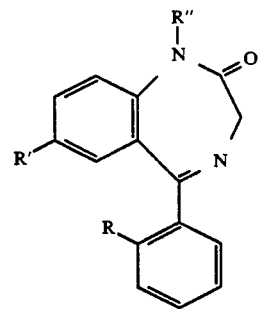

where R is —F, —Cl where R' is —H, —Cl, —NO$_2$ where R" is a linking group comprising one of the following;

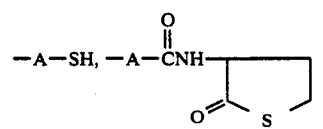

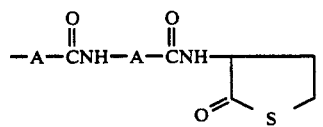

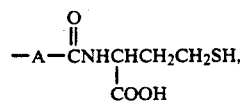

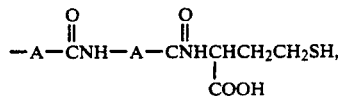

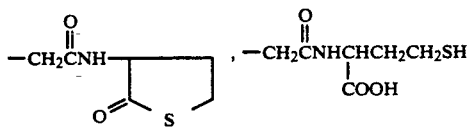

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

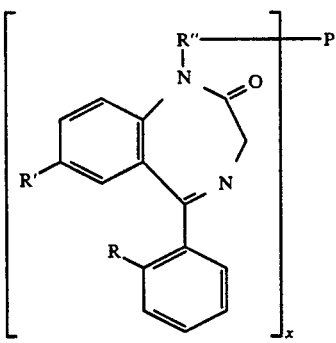

where P is an antigenic protein or polypeptide or a protein, polypeptide or label;
wherein x is at least one and not greater than 100;
where R is —F, —Cl
where R' is —H, —Cl, —NO$_2$
where R" is a linking group of the following:

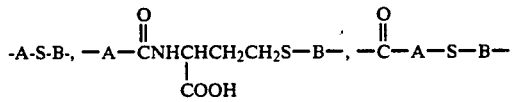

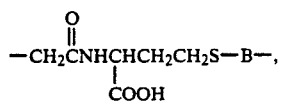

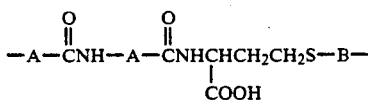

where A is a linking group of from 1 to 20 carbons and 0 to 10 heteratoms (NH, O, S) either branched or straight chain;
where B is a linking group ultimately attached to a protein, polypeptide or label selected from the group comprising:

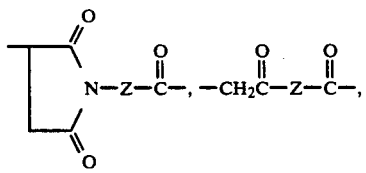

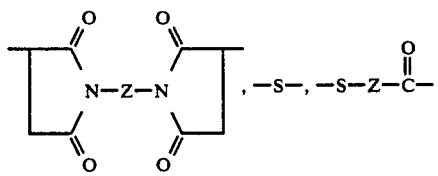

where Z is a linking of from 1 to carbons and 0 to 10,heteratoms (NH, O, S) and may be branched or straight chain.

In general, the compounds of this invention also have the following formula:

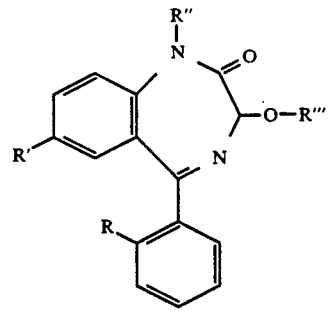

where R is —F, —Cl
where R' is —H, —Cl
where R" is —H, —CH$_3$
where R'" is a linking group comprising:

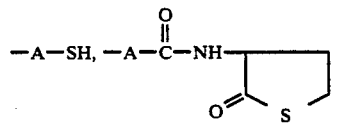

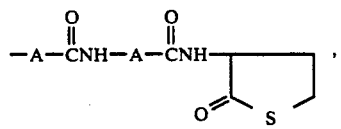

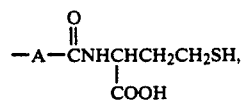

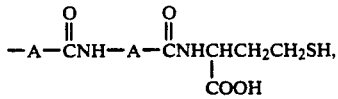

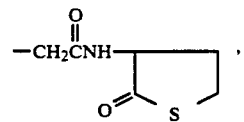

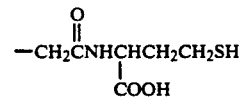

where A is a linking group of from 1 to 20 carbons and from 0 to 10 heteroatoms (NH, O, S), either branched or straight chain.

Also, in addition, the general form of the immunogenic protein or polypeptide molecule or the protein or polypeptide molecule or label derivatized via an amide, disulfide, thioether, or ester bond to the molecule or label to a compound of the formula is of the following:

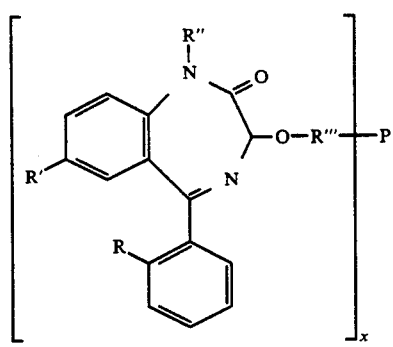

where P is an antigenic protein or polypeptide or a protein, polypeptide or label;

where x is at least one and not greater than 100;

where R is —H, —Cl where R' is —H, —Cl where R" is —H, —CH₃ where R''' is a linking group of the following:

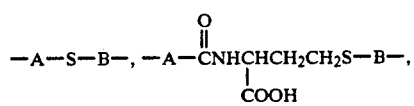

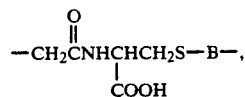

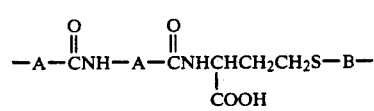

where A is a linking group of from 1 to 20 carbons and 0 to 10 heteroatoms (NH, O, S) either branched or straight chain;

where B is a linking group ultimately attached to a protein, polypeptide or label selected from the group comprising:

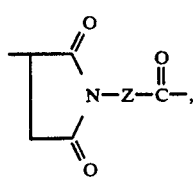

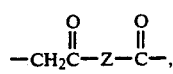

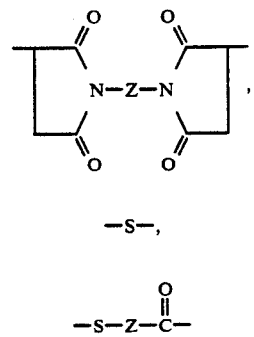

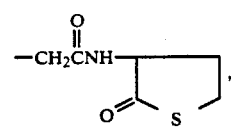

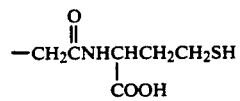

where Z is a linking group of from 1 to 20 carbons and 0 to 10 heteroatoms (NH, O, S) and may be branched or straight chain.

The preferred compounds (best mode) of this invention have the following formula:

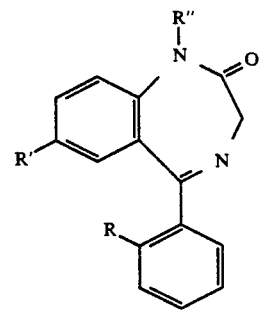

where R is —F, —Cl where R' is —H, —Cl, —NO₂ where R" is a linking group comprising one of the following;

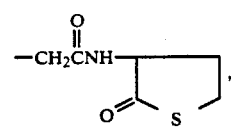

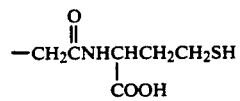

where A is a linking group of from 1 to 20 carbons and from 0 to 10 heteroatoms (NH, O, S), either branched or straight chain.

In addition, the form of the preferred (best mode) immunogenic protein or polypeptide molecule or the protein or polypeptide molecule or label derivatized via an amide or ester bond to the molecule or label to a compound of the formula is of the following:

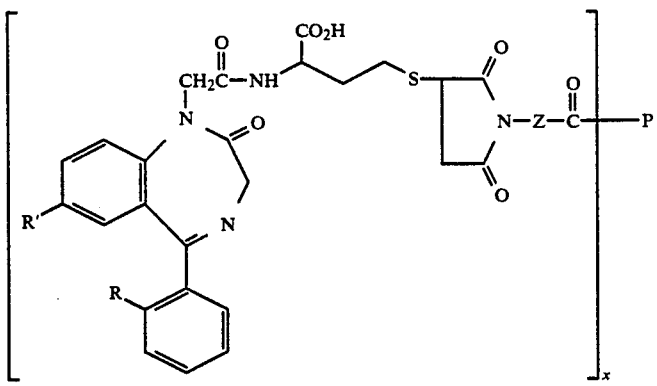

where P is an antigenic protein or polypeptide or a protein, polypeptide or label;
where x is at least one and not greater than 100;
where R is —F, —Cl
where R' is —H, —Cl, —NO$_2$
where Z is a linking group of from 1 to 20 carbons and 0 to 10 heteroatoms (NH, O, S) and may be branched or straight chain.

The preferred (best mode) compounds of this invention also have the following formula:

-continued

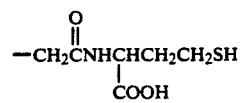

In addition, the form of the preferred (best mode) immunogenic protein or polypeptide molecule or the protein or polypeptide molecule or label derivatized via an amide or ester bond to the molecule or label to a compound of the formula is of the following:

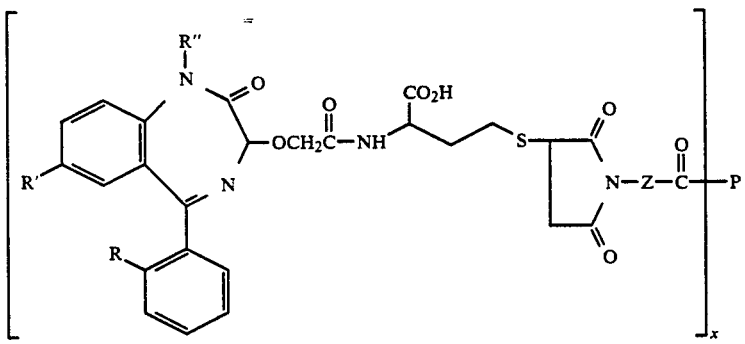

where P is an antigenic protein or polypeptide or a protein, polypeptide or label;
where x is at least one and not greater than 100;
where R is —F, —Cl
where R' is —Cl
where R" is —H, —CH$_3$
where Z is a linking group of from 1 to 20 carbons and 0 to 10 heteroatoms (NH, O, S) and may be branched or straight chain.

Of particular interest are the water soluble benzodiazepine derivatives described herein. The hydrophobic nature of the benzodiazepine molecule causes it to adsorb to plastic and glass surfaces and to proteins. Thus, the benzodiazepine derivatives of the present invention are synthesized such that a carboxylic acid group is introduced into the molecule to improve the water solubility of the derivative. This is particularly important because when immunogens and protein conjugates are prepared a number of benzodiazepine derivatives, roughly 1-100, are covalently attached to the protein, polypeptide or label. The high degree of substitution can cause the precipitation of the protein or polypeptide conjugate or label if additional water solubiliz-

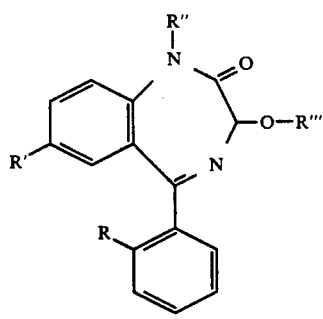

where R is —F, —Cl
where R' is —Cl
where R" is —H, —CH$_3$
where R'" is a linking group comprising one of the following;

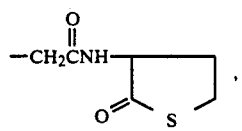

ing groups, for example, carboxylic acids and sulfonic acids, are not incorporated into the benzodiazepine derivative. In addition, in the absence of water solubilizing groups on the benzodiazepine molecule the benzodiazepine derivative which is covalently attached to the protein or polypeptide can adsorb to the protein surface or can interact with each other at the protein surface and can result in fewer benzodiazepine derivatives available to bind the receptor. Thus, when the covalently attached benzodiazepine derivatives interact with each other or are adsorbed to the protein or polypeptide surface the binding affinity of the receptor for the conjugate is decreased. In general, for immunoassays, the highest possible binding affinity is preferred because this allows for a sensitive and rapid immunoassay (for example, see U.S. Pat. Nos. 5,028,535 and 5,089,391). The novel benzodiazepine derivatives described herein provide improved water solubility.

The benzodiazepines used for the synthesis of the derivatives described by the Examples herein are the N-desalkyl flurazepam and lorazepam. These derivatives were used because of the available amide nitrogen and the 3' hydroxyl for use in synthesizing the chemical linking group. One skilled in the art can recognize that other benzodiazepines with an amide nitrogen capable of performing a nucleophilic attack, such as clonazepam, oxazepam, lorazepam and bromazepam can also result in N-alkylated derivatives as taught herein. Also, benzodiazepines possessing a 3' hydroxyl, for example, oxazepam and temazepam can be derivatized at the 3' hydroxyl as taught herein.

The benzodiazepine derivatives are also synthesized as thiols or thiol esters so that their covalent attachment to proteins, polypeptides or labels can easily be performed under mild conditions, for example, pH 7 in a protein solution. The linking arm between the drug derivative and the thiol or thiol ester can be of various lengths. For example, the carboxylic acid benzodiazepine derivatives as described herein can be reacted with, for example, homocysteine thiolactone. Also, the carboxylic acid benzodiazepine derivative can first be reacted with varying chain lengths of an aminoalkyl carboxylic acid ester, for example, 4-aminobutyric acid methyl ester, the ester can then be hydrolyzed in mild base and the resulting carboxylic acid benzodiazepine derivative can further be reacted with an amino alkyl-thiol ester, such as, homocysteine thiolactone. The thiol esters are hydrolyzed in dilute base, for example, 0.01 M-0.1 M potassium hydroxide, to generate the thiol group which is reacted with the thiol reactive group, such as a maleimide, an alkyl halide or a thiol. The thiol reactive group is generally on the protein, polypeptide or label but can also be incorporated onto the protein, polypeptide or label after the thiol drug reacts with the thiol reactive compound.

The protein, polypeptide or label is reacted with a reagent which incorporates a maleimide or alkylhalide into the molecule. These reagents and methods for their use are available from Pierce, Rockford, IL, for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol, but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the benzodiazepine thiol derivatives. Conversely, the bis-maleimide compound can be reacted with the thiol derivative and subsequently to the thio containing protein, polypeptide or label. Common bis-maleimides are bis-maleimidohexane from Pierce, N,N'-bis (3-maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wisc. The thiol benzodiazepine derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,046,636, 4,243,654, 5,028,535 and 5,089,391.

EXPERIMENTAL EXAMPLES

Example 1

Synthesis of N—Carboxymethylflurazepam

N-Desalkylflurazepam (1.0 g, $3.5 \times 10^{-3}$ mol, Alltech Assoc., Deerfield, Ill.) was dissolved in anhydrous dimethylformamide (35 ml). Finely powdered anhydrous potassium carbonate (0.54 g, $3.9 \times 10^{-3}$ mol) was added to the solution followed by ethyl bromoacetate (0.65 g, $3.9 \times 10^{-3}$ mol). The flask was purged with argon and stirred at room temperature for 24 h. The solvent was removed in vacuo to give a yellow oily residue. Ethanol (45 ml) was added to the residue followed by deionized water (35 ml). Potassium hydroxide solution (1 N, 9 ml) was added and stirred at room temperature for 1 h. Ethanol was removed in vacuo. The aqueous solution was then acidified to pH 3.0 with hydrochloric acid (6 N). Diethyl ether (50 ml) was added to the acidified solution. The organic layer was extracted with deionized water ($2 \times 40$ ml) and dried over anhydrous magnesium sulfate. The drying agent was removed by filtration and the solvent was removed in vacuo to give 0.9 g yellow precipitate as the product.

Example 2

Synthesis of N-[2-(2-Amino-4-Thiolbutanoic Acid Thiolactone)-Acetamide]-Flurazepam N—Carboxymethylflurazepam (0.9 g, $2.6 \times 10^{-3}$ mol) was dissolved in anhydrous dimethylformamide (30 ml). dl-Homocysteine thiolactone hydrochloride (0.44 g, $2.9 \times 10^{-3}$ mol) was added to the solution followed by anhydrous (0.48 g, $6.1 \times 10^{-3}$ mol), and 1-(3-dimethylaminopyridine propyl)-3-ethylcarbodiimide hydrochloride (0.59 g, $3.1 \times 10^{-3}$ mol) The flask was then purged with argon and stirred at room temperature for 2 h. The solvent was removed in vacuo, and ethyl alcohol (20 ml) was added to azeotrope any residual dimethylformamide. The residue was partitioned between 0.5 M potassium phosphate pH 7.0 (40 ml) and ethyl acetate (40 ml). The organic layer was washed with deionized water (40 ml$\times$1) and dried over anhydrous magnesium sulfate. The drying agent was removed by filtration, and the solvent removed in vacuo. Diethyl ether (20 ml) was added to the residue, and the solution was then filtered to give 0.8 g of pink precipitate as the final product.

Example 3

Synthesis of N-(Cysteine)Acetamide-Flurazepam

N-[2-(2-Amino-4-thiolbutanoicacidthiolactone)acetamide]-flurazepam (0.01 g, $2.2 \times 10^{-5}$ mol) was dissolved in 0.67 ml dimethylformamide/water (70/30, v/v). Potassium hydroxide (0.45 ml, 0.25 N) was added and the solution sat at room temperature for 30 sec. Potassium phosphate buffer (0.11 ml, 0.5 M, pH 7), was immediately added and the solution was adjusted to pH 7-7.5 with hydrochloric acid (1 N). The title compound in solution was used as is to react with thiol reactive groups, such as maleimides, alkyl halides or thiols, which are either free in solution or are coupled to proteins, polypeptides or labels.

Example 4

Synthesis Lormetazepam

To a stirring solution of lorazepam (3.21 g, $1.0 \times 10^{-2}$ mol) in anhydrous dimethylformamide (100 ml) was added anhydrous powdered potassium carbonate (1.52 g, $1.1 \times 10^{-2}$ mol) followed by iodomethane (0.69 ml, $1.1 \times 10^{-2}$ mol). The mixture was stirred at room temperature for 20 hours. The solvent was evaporated under vacuum, the residue was treated with water (100 ml) and was stirred at room temperature for 2 hours. The resulting fine light yellow solid was collected by filtration and was dried under vacuum to afford 3.3 g (98%) of lormetazepam as a pale yellow solid: m.p. 201°-203° C. .

Example 5

Synthesis of O-Carboxymethyllormetazepam

Lormetazepam (3.3 g, $9.8 \times 10^{-3}$ mol) was treated with thionyl chloride (40 ml, $5.5 \times 10^{-1}$ mol) and the resulting solution was refluxed with stirring for 1 hour. The excess thionyl chloride was removed by addition of toluene (120 ml) and distillation until the stillhead temperature reached 110° C. The solution was allowed to cool and the residual solvent was treated with methyl glycolate (8 ml, $1.0 \times 10^{-1}$ mol) and the mixture Was stirred at 90° C. for 30 minutes when a red, homogenous solution was obtained. After cooling, the excess methyl glycolate was evaporated under vacuum and the residue was treated with methyl alcohol (50 ml). The resulting solution was then treated with 1 N potassium hydroxide solution (50 ml) and after stirring for one minute the solution was evaporated to low volume under vacuum. The residual solution was treated with water (60 ml), washed with diethyl ether (2×60 ml) and acidified to pH 2-3 by dropwise addition of 6 N hydrochloric acid (8 ml). The mixture was treated with diethyl ether (50 ml) and stirred at room temperature for 1 hour. The resulting precipitate was collected by filtration, washed with water (30 ml), diethyl ether (30 ml) and was dried under vacuum to afford 1.3 g (34%) of O-Carboxymethyllormetazepam as an off-white solid.

Example 6

Synthesis of 3-O-[2-(2-Amino-4-Thiolbutanoic Acid Thiolactone)-Acetamide]-Lormetazepam To a stirring solution of O-carboxymethyllormetazepam (1.3 g, $3.3 \times 10^{-3}$ mol) and dl-homocysteine thiolactone hydrochloride (0.6 g, $3.9 \times 10^{-3}$ mol) in anhydrous dimethylformamide (25 ml) was added anhydrous pyridine (0.66 ml, $8.2 \times 10^{-3}$ mol) followed by 1-(3-dimethylaminopropyl)-3-ethylcarbodiimide hydrochloride (0.82 g, $4.3 \times 10^{-3}$ mol). The mixture was stirred under argon at room temperature for 6 hours. The solvent was evaporated under vacuum and the residue evaporated twice from ethyl alcohol (20 ml). The residue was treated with 0.5 M potassium phosphate/0.1 M potassium borate buffer at pH 7 (20 ml) and extracted with ethyl acetate (2×40 ml). The combined organic layers were washed with water (20 ml), dried over anhydrous magnesium sulfate and filtered. The filtrate was evaporated under vacuum and the residue treated with diethyl ether (15 ml) to yield a solid which was collected by filtration to afford 1.55 g (95%) of 3-O-[2-(2-amino-4-thiolbutanoic acid thiolactone)-acetamide]-lormetazepam as a beige solid.

Example 7

Synthesis of 3-O-[(Cysteine)Acetamide]-Lormetazepam

3-O-[2-(2-Amino-4-thiolbutanoic acid thiolactone)acetamide]-lormetazepam (0.01 g, $2.0 \times 10^{-5}$ mol) was dissolved in 0.41 ml dimethylformamide then 0.51 ml water was added. Potassium hydroxide (0.1 ml, 1 N) was added and the solution sat at room temperature for 1 min. Potassium phosphate buffer (0.2 ml, 0.5 M, pH 7), was immediately added and the solution was adjusted to pH 7-7.5 with hydrochloric acid (1 N). The title compound in solution was used as is to react with thiol reactive groups, such as maleimides, alkyl halides or thiols, which are either free in solution or are coupled to proteins, polypeptides or labels.

We claim:

1. A compound of the formula:

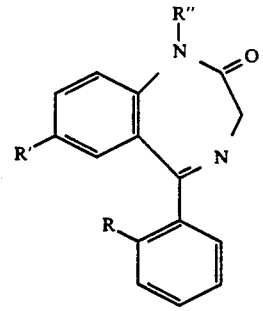

where R is -F, —Cl
where R' is —H, —Cl, —NO$_2$
where R" is a linking group consisting of one of the following;

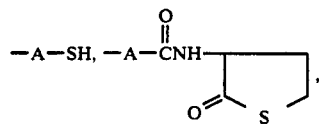

-continued

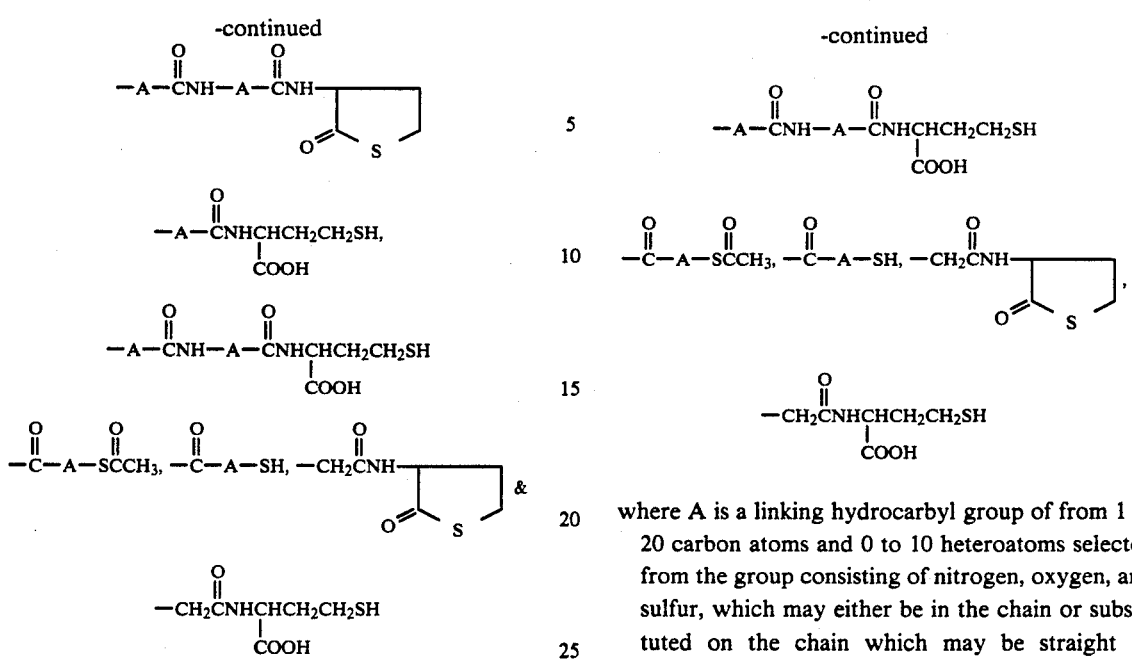

&

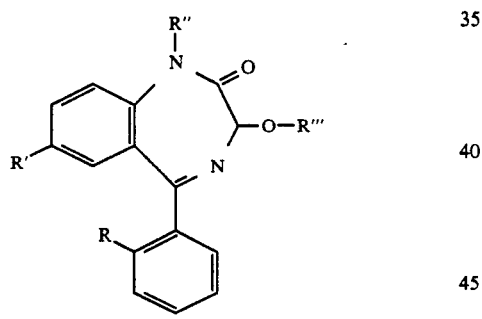

where A is a linking hydrocarbyl group of from 1 to 20 carbon atoms and 0 to 10 heteroatoms selected from the group consisting of nitrogen, oxygen, and sulfur, which may either be in the chain or substituted on the chain which may be straight or branched.

2. A compound of the formula:

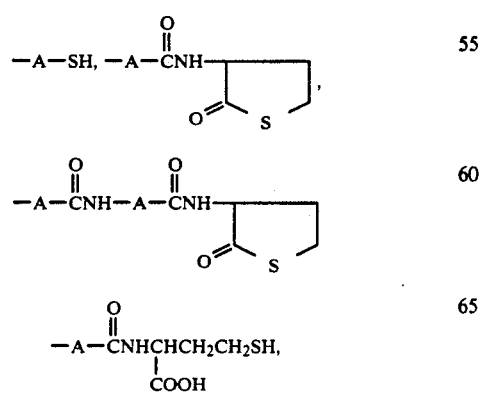

where R is —F, —Cl
where R' is —H, —CL
where R" is —H, —CH$_3$
where R''' is a linking group consisting of one of the following:

-continued where A is a linking hydrocarbyl group of from 1 to 20 carbon atoms and 0 to 10 heteroatoms selected from the group consisting of nitrogen, oxygen, and sulfur, which may either be in the chain or substituted on the chain which may be straight or branched.

3. A compound of the formula:

where R is —F, —Cl
where R' is —H, —Cl, —NO$_2$
where R" is a linking group consisting of one of the following:

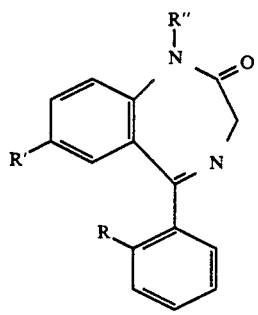

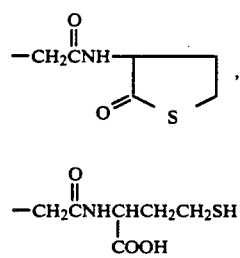

where A is a linking hydrocarbyl group of from 1 to 20 carbon atoms and 0 to 10 heteroatoms selected from the group consisting of nitrogen, oxygen, and sulfur, which may either be in the chain or substituted on the chain which may be straight or branched.

4. A compound of the formula:

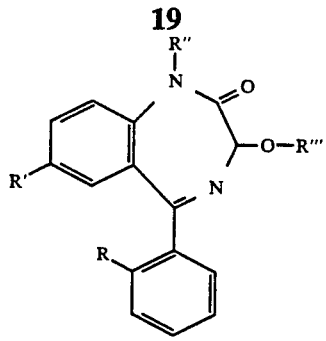
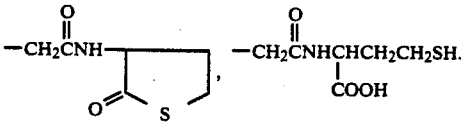
where R is —F, —Cl
where R' is —Cl
where R" is —H, —CH₃
where R''' is a linking group consisting of one of the following:
* * * * *